(12) United States Patent
Sjogren et al.

(10) Patent No.: US 7,892,571 B2
(45) Date of Patent: Feb. 22, 2011

(54) CONTROLLED RELEASE OF S-METHOPRENE AND OTHER ACTIVE INGREDIENTS WITH ACTIVATED CARBON

(75) Inventors: Robert D. Sjogren, Ladera Ranch, CA (US); David R. Sjogren, Sherwood, OR (US)

(73) Assignee: Wellmark International, Schaumburg, IL (US)

( * ) Notice: Subject to any disclaimer, the term of this patent is extended or adjusted under 35 U.S.C. 154(b) by 977 days.

(21) Appl. No.: 11/064,442

(22) Filed: Feb. 23, 2005

(65) Prior Publication Data

US 2006/0188572 A1 Aug. 24, 2006

(51) Int. Cl.
*A01N 25/08* (2006.01)
(52) U.S. Cl. .................. 424/409; 424/408; 424/421; 424/404; 424/489
(58) Field of Classification Search .................. None
See application file for complete search history.

(56) References Cited

U.S. PATENT DOCUMENTS

| | | | |
|---|---|---|---|
| 4,631,857 A | 12/1986 | Kase et al. | |
| 4,732,762 A * | 3/1988 | Sjogren | 424/409 |
| 4,774,090 A * | 9/1988 | Fekete et al. | 424/408 |
| 4,876,091 A * | 10/1989 | Clarke, Jr. | 424/421 |
| 4,971,796 A * | 11/1990 | Sjogren | 424/417 |
| 5,484,600 A | 1/1996 | Sjogren | |
| 5,747,054 A | 5/1998 | Yang et al. | |
| 5,858,386 A | 1/1999 | Levy | |
| 6,143,313 A | 11/2000 | Ito et al. | |
| 6,391,329 B1 | 5/2002 | Ito et al. | |
| 6,512,012 B1 | 1/2003 | Levy | |
| 6,521,670 B1 | 2/2003 | Forsythe et al. | |
| 6,551,560 B1 | 4/2003 | Flashinski et al. | |
| 6,676,954 B2 | 1/2004 | Dai et al. | |
| 7,163,687 B1 * | 1/2007 | Murphy et al. | 424/410 |
| 7,196,116 B1 * | 3/2007 | Wilkins et al. | 514/549 |
| 2004/0195182 A1 * | 10/2004 | Elliott | 210/681 |

OTHER PUBLICATIONS

Kirk-Othmer Encyclopedia of Chemical Technology, vol. 4 (e-book edition), Wiley , 2001, pp. 742 and 751.*
"Altosid® Briquets. A Sustained Release Mosquito Growth Regulator to Prevent Adult Mosquito Emergence," Wellmark International, 2 pages (Jan. 2002).
"Altosid® Liquid Larvicide Concentrate," Wellmark International, 1 page (Apr. 2004).
"Altosid® Liquid Larvicide Concentrate. Prevents Adult Mosquito Emergence (Including those which may Transmit West Nile Virus)," Wellmark International, 2 pages (Feb. 2003).
"Altosid® Liquid Larvicide Mosiquito Growth Regulator," Wellmark International, 1 page (Apr. 2004).
"Altosid® Liquid Larvicide Mosquito Growth Regulator. Prevents Emergence of Adult Floodwater Mosquitos," Wellmark International, 2 pages (May 2003).
"Altosid® Pellets Mosquito Growth Regulator. A Granular Product to Prevent Adult Mosquito Emergence," Wellmark International, 2 pages (Nov. 1999).
"Altosid® SBG. An Insect Growth Regulator for Applications to Single Broods of Mosquito Larvae to Prevent Adult Mosquito Emergence," Wellmark International, 2 pages (Apr. 2000).
"Altosid® XR Extended Residual Briquets. A Sustained Release Product to Prevent Adult Mosquito Emergence (Including those which may Transmit West Nile Virus)," Wellmark International, 2 pages (Apr. 2003).
"Altosid® XR-G. An Extended Residual Granular Product to Prevent Adult Mosquito Emergence (Including those Mosquitos which may Transmit West Nile Virus)," Wellmark International, 2 pages (Jun. 2003).
"Aquaprene™ Flex Granules. A Sustained Release Granular Product—Prevents Adult Mosquito Emergence for up to 80 Days Depending on Application Rate (Including those which may Transmit West Nile Virus)," Adapco, 2 pages (Date Unknown).
"Aquaprene™ Tossits. Water Soluble Pouch Prevents Adult Mosquito Emergence in Areas up to 1/8 Acre (5,445 ft$^2$) from a Single Application Point," Adapco, 2 pages (Date Unknown).
"Aquaprene™ WP. Wettable Powder Prevents Adult Mosquito Emergence When Applied Pre or Post-Hatch (Including those which may Transmit West Nile Virus)," Adapco, 2 pages (Date Unknown).
Case, T. et al., "Effects of the growth regulator methoprene on *Culex tarsalis* and non-target organisms in California rice fields," *Mosquito News*, vol. 38, No. 2, pp. 191-196 (Jun. 1978).
Imai, C. et al., "Efficacy of several larvicides in laboratory and field tests against *Anopheles sundaicus* in a village, North Sumatra, Indonesia," *Jpn. J. Sanit. Zool.*, vol. 38, No. 2, pp. 93-102 (1987).
Kamei, M. et al., "Concentration and Residual Efficacy of Methoprene in a Running Ditch," *Journal of Pesticide Science*, vol. 17, No. 3, pp. 155-159 (Aug. 1992).
Nelson, M. et al., "Field trials with the insect growth regulator OMS-1697 (Altocid, Methoprene) against Culex Pipiens Fatigans in Jakarta, Indonesia," *World Health Organization*, pp. 1-9 (Mar. 29, 1976).
Schaefer, C. et al., "Evaluation of new chemicals as mosquito control agents," pp. 75-77 (Date Unknown).
Self, L. et al., "Field trials with two insect growth regulators against *Culex quinquefasciatus*," *Mosquito News*, vol. 38, No. 1, pp. 74-80 (Mar. 1978).

(Continued)

*Primary Examiner*—Robert A Wax
*Assistant Examiner*—Hasan S Ahmed
(74) *Attorney, Agent, or Firm*—Kilpatrick Townsend & Stockton

(57) ABSTRACT

An effective controlled release pest control composition can use activated carbon as the sole release agent. Liquid pesticide is adsorbed into the interior mesopore and macropore space of the activated carbon. Upon contact with water, the pesticide is slowly displaced from the carbon into the environment for appropriate control. The particulate can be used as is or can be combined with liquid or solid diluents. The particle can be formed into larger composites comprising a granule, a pellet, and an agglomerated particle, etc. A variety of pesticides can be used including insecticides, herbicides, fungicides, growth regulators, etc.

29 Claims, No Drawings

OTHER PUBLICATIONS

Spencer, J. et al., "Potential effectiveness of two commercial formulations of methoprene for floodwater mosquito control in the Texas Coastal Zone," *The Southwestern Entomologist*, vol. 4, No. 2, pp. 117-124 (Jun. 1979).

Buéi, K. et al., "The Effect of a Juvenile Hormone Mimic, Methoprene, Against Mosquito Larvae," *Jap. J. Sanit. Zool.*, vol. 26, Nos. 2-3, pp. 105-111 (1975) (Summary in English only).

Ishii, T. et al., "Field Trials Using Altosid® 10F Growth Regulator Against *Culex pipiens Pollens* (Diptera: Culicidae) of Tokushima, Japan," *Jap. J. Sanit. Zool.*, vol. 36, No. 2, pp. 65-75 (1987) (Summary in English only).

Toma, T. et al., "Effects of Methoprene, a Juvenile Hormone Analogue, on Mosquito Larvae from the Ryukyu Archipelago, Japan," *Jap. J. Sanit. Zool*, vol. 41, No. 2, pp. 99-103 (1990) (Summary in English only).

T.G. Floore, et al.; Efficacy Studies of Aquaprene etc.; Journal of the American Mosquito Control Association; 2007; 23(2):187-189.

Quistad et al.; Environmental Degradation of the Insect Growth Regulator Methoprene (Isopropyl); J. Agr. Food Chem.; 1975; vol. 23, No. 2; pp. 299-303.

Troeh/Donahue; Dictionary of Agricultural and Environmental Science; Iowa State Press; p. 5.

Rhodia, Inc. Material Safety Data Sheet; GEROPON SS-O-75/CAN; http://rio/msds/files/000008882000010001E00017.HTM.

Science Lab.com, Inc.; Material Safety Data Sheet—Aerosol OT-75% MSDS.

Henrick, Clive, et al.; Investigation of the Relationship Between s-Methoprene and Deformities in Anurans; Jour. of the American Mosquito Control Assn.; 2002; 18(3):214-221.

* cited by examiner

CONTROLLED RELEASE OF S-METHOPRENE AND OTHER ACTIVE INGREDIENTS WITH ACTIVATED CARBON

FIELD OF THE INVENTION

Controlled release pesticide compositions and pest control means can be distributed throughout the environment. Effective pest control and environmental management can be achieved. Pest control means can release a pesticide at effective concentrations for a predetermined time period. Economical and effective active ingredient concentrations can be used to obtain pest control with safe environmentally friendly active agents and absorbents or carriers.

BACKGROUND OF THE INVENTION

Controlled release S-methoprene pesticide can offer advantages for pest control since the control materials can be released when needed and in controlled or effective amounts. The invention relates to the control of aquatic pests that can emerge into adult flying insect pests in an aquatic location where pests hatch, mature and subsequently enter the terrestrial environment. The aquatic locations of the invention are often wet year around or are locations that are often dry, but can become episodically flooded creating a pestiferous aquatic location. If the periodic flooding of such dry areas result in a pest generating volume of water (about 1 cm or greater standing water) for a sufficient period of time (4 days at a minimum), the flooded area can create periodic populations of flying insect pests during the spring, summer and fall of the year. The treatment of aquatic breeding sites or loci involves the careful application of a control agent to the aqueous environment. A variety of aqueous control agents have been created. Sjogren, U.S. Pat. Nos. 4,732,762 and 4,971,796 disclose a briquette, granular or particulate form of a slow release pest control agent. The briquette form of the pest control agent comprises a cast, high compressive strength, plaster briquette that can slow the release of the pest control agent into the aqueous environment based on the dissolution rate of the high compressive strength plaster. The briquette can contain the pest control agent in a combination with a number of other ingredients that can stabilize the agent and to obtain a sustained level of controlled release. The granular form comprises a core, a coating and an effective amount of the pest control agent. Such a granular form can be distributed into the general environment including aquatic and dry aquatic sites. Levy, U.S. Pat. Nos. 5,858,386 and 6,512,012 teach enhancing the action of conventional pest control agent with a designed formulation using a surface filming material.

The Metropolitan Mosquito Control District of Minnesota has used the briquette form of the mosquito control agent by Sjogren. That technology has been licensed to Wellmark International to sell to other governmental agencies in the United States and elsewhere. In large part, these patents relate to the continuous, generally broadcast application over an aquatic surface of a pellet, powder, foam, spray, briquette or other material at a rate of about 2.5 to 20 pounds of treatment material per acre. The briquette is selectively placed in an aquatic site for mosquito control purposes. The patent suggests that the application of the briquette in a carefully placed location in an amount of about 1 briquette per each 200 square feet (6 square meters) of aquatic location at a treatment rate of about 200-400 grams of S-methoprene per acre or 4000 meters$^2$ (about 0.02 to about 0.05 gram/meter$^{-2}$) of an aqueous site.

Controlled release technology developments have recently occurred in many areas. Both macro and micro-encapsulation processes have been used. Capsules of ceramics, biodegradable polymers, porous supports, cellulosic derivatives, urethane compounds, plaster, gypsum and other supports have been made to separate the pesticide from the environment and to ensure a controlled release.

An effective pest control concentration is defined as that amount effective to kill greater than 50% of at least one form or stage of a pest in its life cycle, or a concentration effective to prevent development or maturation of a form or stage of the pest during its life cycle. The pesticide should be released by the pest control means at a rate such that an effective amount is released but little is wasted. Further, the pesticide composition and means should comprise natural materials, be non-toxic and biodegradable, and of low cost. Accordingly, a substantial need exists for a controlled release formula that is inexpensive, can deliver controlling concentrations for a useful period of time, typically for least 4 days, at least 30 days or for 40 to 120 days.

BRIEF DISCUSSION OF THE INVENTION

The invention relates to unique, absorbent based, slow release pest control composition and to methods of applying the pest control composition to periodically flooded areas to obtain substantial pest control during flooded periods. A careful calculation of the amount of slow release material and the careful introduction of the material into the dry location can successfully control flying insects during the period of year during which temperatures permit hatching, maturing and emergence of flying insect pests.

S-methoprene [isopropyl-(2E,4E,7S)-11-methoxy-3,7,11-trimethyl-2,4-dodecadienoate] is a preferred pesticide. The material can effectively control insect maturation with no environmental or adverse human impact.

Activated carbon can be formulated with an organic pesticide such as S-methoprene in an effective controlled release material. A solid, slow release, carbon particulate with a mosquito control composition can be distributed into a wet or dry treatment locus. Dry locus can be periodically flooded and can be periodic pest emergence locations. The compositions of the invention can be added to the dry locale in a dry form and can release pest control material slowly over a period at least 4 days, at least 20 days, for 40 to 120 days or for a pest season (20 to 45 weeks). The control material can provide a treatment locus with effective control and attain a substantial concentration of pest control agent such as S-methoprene that can range from about 0.2 parts per billion to 1390 parts per billion of the active agent. Such amounts can achieve effective control in the prevention during episodes of periodic flooding. The pest control composition typically comprises an absorbent carbon composition containing about 10 to about 50 wt % of the S-methoprene pest control agent. Such a slow release composition, when contacted with water, slowly releases the S-methoprene into the aqueous environment in direct proportion to the amount of S-methoprene absorbed onto the carbon particulate. The materials of the invention can be engineered to release for a defined period of time ranging from at least 4 days, at least 30 days, at least about 40 to 120 days or a substantial control season depending on the amount of S-methoprene absorbed onto the carbon and applied to a field mosquito breeding site. For this purpose, the carbon composition can contain about 50 to about 200 grams of methoprene per kilogram of carbon, 100 to about 500 grams of methoprene per kilogram of carbon or about 500 to about 1000 grams of methoprene per kilogram of carbon for the extent of pest control desired. Whole S-methoprene is the preferred material the control composition can contain other pesticides and related materials but no other solid absorbent, adsorbent or controlled release matrix materials like carbon.

The S-methoprene and carbon treatment material of the invention can be applied to both wet or flooded sites, to dry or unflooded sites or to sites that are intermittently wet. In wet sites and intermittent sites when wet, the partition coefficient of water and S-methoprene releases the control agent into the aqueous site to effectively control emergence of insect pests. Whether used in the flooded site or in the dry site, the degree of kill or emergence prevention obtained by the active agent is generally proportional to the amount of material applied. This is a surprising result since ordinarily with insect control materials; the control ability of the agent tends to drop off as the concentration is increased. Within the operating range of the materials of the invention, the active agent obtains proportionally increased control as the amount applied is increased.

Such slow release carbon S-methoprene is free of other slow release matrices. The particulate carbon adsorbs the pesticide into the carbon structure to form a particulate capable of releasing the S-methoprene into the locus when wet. The carbon in the locus contacts water and pesticide is slowly released. Activated carbon is used due to its high surface area and effective loadings of S-methoprene. Carbon particle sizes obtain uniform particle distribution over large areas of the environment. The ratio of water exchange obtains effective release rates. The combination of activated carbon particulate and S-methoprene has a unique controlled release rate effective for mosquito control. The novel controlled release combination requires only carbon with absorbed S-methoprene and uniform distribution of the carbon particulate to achieve the controlled release and mosquito control. S-methoprene is adsorbed into activated carbon by slowly contacting a neat or a low viscosity concentrate of an active carbon. A powder blender such as a ribbon blender can distribute the active ingredient for purposes of uniformly adsorbing or absorbing the liquid into the carbon powder. Carbon particulate evenly distributed into the environment came into contact with water. A solvent action displaced the S-methoprene into the aqueous environment.

Controlled release carbon particulate with S-methoprene substantially free of a second matrix can be used for mosquito control. The invention is limited to a particulate activated carbon and S-methoprene in the particulate. After being applied in the field, the particulate comes in contact with environmental water, slowing releasing an effective controlling amount of S-methoprene.

A neat, concentrated or dilute pesticide is used with the carrying capacity of activated carbon to form powder, granule or pellet particles, suitable for application in the field. S-methoprene may be absorbed into the carbon in powder, granule or pellet form or the resulting particulate powder can be formed into granules, pellets or agglomerates into larger particles. Controlled S-methoprene concentrations are achieved in the environment. Reduced active ingredient release accomplishes pest control for the desired time interval. Maintenance of threshold chemical concentrations needed to control to achieve the desired target effect is reduced.

The slow or controlled release formulation uses activated carbon and absorbed S-methoprene. S-methoprene is adsorbed into the activated carbon pores directly when an active ingredient is neat or a low viscosity liquid.

The carbon and methoprene can be used (1) alone, (ii) activated carbon S-methoprene with a diluent powder, (iii) carbon S-methoprene particles in a water dispersible form, (iv) a prilled powder, (v) powder, prilled on a solid core with an inorganic water soluble binder, (vi) activated carbon granules (crushed activated charcoal particles), shapes, extruded or compressed activated carbon pellets, briquettes or blocks optionally in combination with other active ingredients, solvents and adjuvants, etc.

Carbon is an efficient light and UV absorber that can protect against the damaging effects of ultra violet light. UV radiation (wave length less than 300 nm) can cause degradation of S-methoprene in the environment. UV degradation requires higher dosage rates than is otherwise required for pest control. An amount needed to achieve the control of the target organism is recognized as means to deliver the optimum controlling concentration of an active ingredient at least cost.

For the purpose of this application, the term "flooded site" refers to either a natural site or a site in the built human environment having a substantially continuous portion of standing water having a depth of greater than 1 centimeter. Such sites must contain sufficient water to trigger the egg hatch, maturation and release of flying insect pests. The term "dry site" refers to a portion of the natural or human built environment having the eggs of the flying insect pest in an inactive form. Such dry sites, when flooded, can activate the eggs of the flying insect pest to promote the hatching, maturation and subsequent emergence of the flying insect pest. Typically, a dry site has no substantial proportion of standing water, but can contain dew or substantial moisture in the absence of the amount of water necessary to trigger hatching. In summary, a "dry site" may contain some water, but contains insufficient water to promote the hatching, maturation and release of flying insect pests.

DETAILED DISCUSSION OF THE INVENTION

A controlled release carbon/S-methoprene composition can consist essentially of a powder particulate, granule, pellet, briquette or block of activated carbon and an adsorbed S-methoprene and a second pest agent or related material. The S-methoprene is adsorbed into carbon pores during product preparation. The invention includes the use of the pesticide composition as a distributed particulate comprising S-methoprene and a solid diluent, a dispersion of S-methoprene in a liquid medium, a pellet or other larger units and extending the activity of a pesticide by adsorbing the liquid pesticide into activated carbon.

Activated carbon is a form of carbon. The particulate obtains a large internal surface area and pore volume of about 500 to 2500 $m^2/g$ or about 750 to 2000 $m^2/g$. Activated carbon is versatile as a result of the size and distribution of the pores. Carbon in the form of powders, agglomerates, granules, and shaped or extruded products meets many needs in mosquito control. Shaped or extruded carbon forms comprise an amount of the carbon particulate in a larger format by casting or extruding an amount of the carbon particulate into a useful absorbable form. Such larger (than the particulate per se) forms can be easier to handle during manufacture and use. Carbon holds S-methoprene by surface attraction or physical adsorption. Physical adsorption is an electrostatic force of attraction (Van der Walls' Forces) between S-methoprene and the surface carbon particulate.

Activated carbon products are rated by activity level, which is usually expressed as total surface area per unit weight in square meters per gram. A secondary indicator of activation level is methylene blue adsorption level expressed in g/100 g. Total exposed surface area will typically be in the range of 100-3000 $m^2/g$, often 250 to 2500 $m^2/g$. Surface area substantially controls the quantity of S-methoprene that can be combined with the particulate and is a factor in the rate of release. Carbon adsorption and release rate depends on the surface area pore size, distribution of pore size and shape. The macroporosity of the carbon is important for the transfer of S-methoprene to adsorption sites within the carbon. Activated carbon surface area determines the amount of activated carbon needed to deliver the pesticide into the environment.

The content of the pesticide which is in the liquid state at room temperature, or converted to the liquid state by heating or use of solvents, to impregnate the activated carbon, powder or granule, is generally 5 to 60 wt % of the carbon, preferably 10 to 50 wt %, more preferably 30 to 40 wt %. For reasons of transferring the impregnated powders in manufacturing, it is advantageous to have an impregnated powder whose surface is sufficiently dry to process without problem, with no added diluent or drying agent. Depending on the nature of the pesticide impregnated and activated carbon used and whether the impregnated carbon is subsequently heated, as the need arises, ambient or at a temperature of 30° to 80° C. S-methoprene is used at 5 and 50 wt %, preferably between 5 and 40 wt %. Preferred particulates have surface areas of about 500 to 2500 $m^2/g$ or about 750 to 2000 $m^2/g$. Most preferred activated carbons can carry the highest pesticide payloads and have activated carbon surface areas of 800 to 1750 $m^2g$. The preferred activated carbon pore sizes are in the micropore range, less than about 2 nm diameter, the more preferred are those which have most pore sizes in the range of about 2-50 nm diameter. A very useful activated carbon has at least some carbon particulate with pores about 2 to 50 nm and greater than 50 nm diameter.

Small activated carbon particle size absorb S-methoprene efficiently. The small particulate is distributed evenly in the environment and release of adsorbed active ingredient into static water conditions. Particles in the 5 to 150 µm range can provide the high water exchange ratios necessary to achieve effective active ingredient concentration. Particles about 0.1 to 10 mm, preferably 0.3-3.0 mm in diameter, granular and shaped or pelleted activated particulate.

Activated carbon can be made from carbon containing materials. For economic reasons, lignite, coal, bones, wood, peat, palm shell and paper mill waste (lignin) are carbon sources. Two basic processes are used depending on the starting raw material and whether a low or high density, powdered or granular carbon is desired. Chemical activation depends upon the action of inorganic chemical compounds, either naturally present or added to the raw material to degrade or dehydrate the organic molecules during carbonization. Gas activation depends upon selective oxidation of the carbonaceous matter with air at low temperature, or steam, carbon dioxide, or flue gas at high temperature. The oxidation is usually preceded by a primary carbonization of the raw material.

Decolorizing carbons are coal and lignite based granules, or light fluffy powders derived from low density starting materials such as sawdust or peat. Many decolorizing carbons are prepared by chemical inactivation. Admixing or impregnating the raw material with chemicals that yield oxidizing gases when heated or that degrade the organic molecules by dehydration usually obtains a decolorizing carbon particulate. In some cases, the chemically activated carbon is given a second activation with steam to impart physical properties not developed by chemical activation.

Active Ingredient

The term "active ingredient" as employed here is intended to include isopropyl-(2E,4E,7S)-11-methoxy-3,7,11-trimethyl-2,4-dodecadienoate (also known as S-methoprene) which is the active ingredient in the composition, available under the trade name Altosid Liquid Larvicide from Wellmark International. Altosid Liquid Larvicide is an insect specific growth regulator that acts to prevent the emergence of adult mosquitoes from the pupae stage by affecting only the maturation of the immature forms of the pest.

The preparation of pesticide-impregnated activated carbon can be done by a variety of means. The essential element is the liquefaction of the pesticidal active ingredient sufficiently for it to penetrate deeply into the pores of the carbon. The process of pesticide liquefaction and loading into activated carbon can be accomplished by numerous means, some of which are:

(1) The addition of low viscosity concentrated liquid technical pesticides, singly or in combination, directly onto or into a moving bed of activated carbon powder, granules or pellets, so as to uniformly distribute the liquid on the surface of the carbon at or below a viscosity which enables it to be drawn into the pores of the carbon by the affinity of the organic compound for activated carbon;

(2) The addition, in small quantity, of an organic solvent chosen for its effectiveness to liquefy a selected crystalline pesticide(s) to be impregnated, to lower the pesticide viscosity followed by its addition onto or into a moving bed of activated carbon powder, granules or pellets, wherein the solvent is left in the activated carbon;

(3) The addition of an organic solvent chosen for its effectiveness in liquefying a selected crystalline pesticide, or pesticides, to be impregnated to convert the pesticide from solid to a low viscosity liquid followed by its addition, in single or multiple liquid pesticide addition steps, or into a moving bed of activated carbon powder, granules or pellets, wherein the pesticide solvent is subsequently evacuated using equipment such as a planetary paddle, heat jacketed, vacuum equipped Ross Mixer.

Preferably, the pesticide is impregnated into the carbon powder with minimum quantity of organic solvent, which is left in the activated carbon. More preferably, the pesticide is impregnated with use of a solvent and the solvent is evacuated from the activated carbon. Most preferably, the S-methoprene is loaded into the activated carbon without the use of a solvent.

S-methoprene absorbed onto suitable activated carbons is typically in concentrated form, resulting in a concentrated pesticide in a small volume. A means of uniformly distributing the combination in the environment is needed. The quantity of S-methoprene incorporated activated carbon powder applied into the environment can range from 8 to 250 gms, preferably 12 to 150 gms, and most preferably 15 to 40 gms. Solid diluents are used in the pesticide industry for both conventional and controlled release formulations.

Less commonly, small quantities of low volatile liquids are used (3 to 128 ounces of liquid/acre) to deliver pesticides. Examples of such liquid diluents are vegetable oils, petroleum oils and polypropylene glycols.

Solid diluents are commonly of two types. Dry powders of 5 to 100 microns and granules of 6 to 60 mesh size. Diluent powders are used to reduce technical powder A.I.s concentrations during manufacture of end use products. Liquid technical pesticides are also sprayed upon powders to transform them to a solid for formulating or handling as were applied by aerial "crop dusters". Examples of low bulk density powders are calcium silicate, diatomaceous earth, Fullers Earth, hydrated alumina and silica gel. High bulk density powders include calcium carbonate, some clays pyrophyllite and talc.

The most common solid diluents used to distribute pesticides in the environment are 6 to 40 mesh particles, i.e. granules. They are termed carriers because they carry or distribute the particle with pesticide in the environment.

Large diluents such as sand, limestone and corncob particles may be coated with a pesticide film. Particulate materials known for their absorptive capacity and high surface area, such as plant fiber granules, diatomaceous earth, and clays can absorb and hold liquid pesticides for application. Activated carbon powder may be blended with plant fiber slurries before prilling, later to be impregnated with a pesticide. Similarly, activated carbon may be prilled on the outside of absorptive conventional carriers during manufacture, and subsequently impregnated during pesticide formulation. The latter two uses provide partial control over pesticide release rate, with that portion of pesticide absorbed into a conventional absorptive carrier being released rapidly, and that portion adsorbed into the activated carbon released slowly over time.

Pesticides formulated on powder diluents may be formed into agglomerated balls, granules or pellets, with or without a core. Powders containing pesticide may be formed into rapidly dissolving granules called Water Dispersible Granules, for addition to water that will be sprayed. Finally, pesticide-containing powders may be extruded with or without other inert ingredients into pellets, or molded into briquettes, balls and numerous other shapes.

All of the above means employ diluents of one type or another. Activated carbon powder impregnated with pesticide described in this invention can be used as part or all, of the diluent in the above-described roles. Thus activated carbon can be used as an adsorptive, and absorptive substrate in place of conventional diluents, or in combination with such diluents in pesticidal formulations. Such diluents serve a valuable function as a means to evenly distribute pesticides in the environment.

Finally, pesticides may be adsorbed into activated carbon powder, granules and pellets of different particulate sizes, and used alone and without use of another diluent, as a means of active ingredient distribution in the environment.

The significance of this invention is in the use of activated carbon as the sole control release agent. The value of the present composition, which requires only activated carbon and an active ingredient, and with some active ingredients a solvent, is the economy, simplicity, and variety of types of commercially useful controlled release formulations that this technology can employ.

EXEMPLARY SECTION

Example 1

A 30% S-Methoprene activated carbon control unit, using 90% S-methoprene technical liquid and Norit HYDRODARCO powdered activated carbon, designed to control mosquitoes for 7 to 80 days depending on dosage applied, was prepared using the following formulation recipe:

| Ingredient | % W/W | Weight (lbs.) |
| --- | --- | --- |
| 90% S-Methoprene Technical | 33.33 | 33.33 |
| Norit HYDRODARCO Activated Carbon | 60.00 | 60.00 |
| Aerosol OT-75 | 6.67 | 6.67 |

Place 60.00 pounds of Norit HYDRODARCO in an appropriately sized ribbon blender. Next, close and turn on the mixer and spray 33.33 pounds of the S-Methoprene technical liquid control material onto the carbon powder with fine spray nozzles. Then, spray Aerosol OT-75 liquid onto the carbon powder. Blend for 10 minutes after spraying is completed. Next jet mill to 10 micron size. Discharge and package the finished powder.

Example 2

A 20% S-Methoprene activated carbon control unit, using 85% S-methoprene technical liquid and Norit SX ULTRA powdered activated carbon, designed to control mosquitoes for 7 to 80 days depending on dosage applied, was prepared using the following formulation recipe:

| Ingredient | % W/W | Weight (lbs.) |
| --- | --- | --- |
| 85% S-Methoprene Technical | 23.53 | 23.53 |
| Norit SX ULTRA Activated Carbon | 69.80 | 69.80 |
| Geropon SS-O-75 | 6.67 | 6.7 |

Place 69.80 pounds of Norit SX ULTRA powder in an appropriately sized ribbon blender. Next, close and turn on the mixer and spray 23.53 pounds of the S-Methoprene technical liquid control material onto the carbon powder with fine spray nozzles. Then, spray Geropon SS-O-75 liquid onto the carbon powder. Blend for 10 minutes after spraying is completed. Next jet mill to 10 micron size. Discharge and package the finished powder.

Example 3

A 40% S-Methoprene activated carbon control unit, using 95% S-methoprene technical liquid and Norit GAC 1240 granular activated carbon, designed to control mosquitoes for 7 to 80 days depending on dosage applied, was prepared using the following formulation recipe:

| Ingredient | % W/W | Weight (lbs.) |
| --- | --- | --- |
| 95% S-Methoprene Technical | 42.10 | 42.10 |
| Norit GAC 1240 Granular Carbon | 51.23 | 51.23 |
| Geropon SS-O-75 | 6.67 | 6.67 |

Place 51.23 pounds of Norit GAC 1240 Granular carbon in an appropriately sized ribbon blender. Next, close and turn on the mixer and spray 42.10 pounds of the S-Methoprene technical liquid control material onto the carbon granules with fine spray nozzles. Then, spray Geropon SS-O-75 liquid onto the granules. Blend for 10 minutes after spraying is completed. Discharge and package the finished powder.

Example 4

A 50% S-Methoprene activated carbon control unit, using 90% S-methoprene technical liquid and Norit CNSP powdered activated carbon, designed to control mosquitoes for 7 to 80 days depending on dosage applied, was prepared using the following formulation recipe:

| Ingredient | % W/W | Weight (lbs.) |
| --- | --- | --- |
| 90% S-Methoprene Technical | 55.55 | 55.55 |
| Norit CNSP Activated Carbon | 37.78 | 37.78 |
| Geropon SS-O-75 | 6.67 | 6.7 |

Place 37.78 pounds of Norit CNSP powder in an appropriately sized ribbon blender. Next, close and turn on the mixer and spray 55.55 pounds of the S-Methoprene technical liquid control material onto the carbon powder with fine spray nozzles. Then, spray Geropon SS-O-75 liquid onto the carbon powder. Blend for 10 minutes after spraying is completed. Next jet mill to 10 micron size. Discharge and package the finished powder.

Experimental Field Trials

Applying S-Methoprene Carbon Powder to Field Mosquito Breeding Sites

Tests of the S-Methoprene Carbon Powder

Pre-Hatch Treatment in Episodically Flooded Field Mosquito Breeding Site

Example 1

Date Treated: Apr. 20, 2004
Location: Bishop, Warm Springs Rd.
Habitat: Irrigated pasture
Species: Ochlerotatus. melanimon
Site Size: 0.25 acre
Treatment: Pre-hatch; sprayed WP on ground
Dosage: 1.5 oz./acre
Water Depth: 6"-12"
Elapsed Days: 29
Sample size: 40
Mortality: 100%

Pre-Hatch Treatment in Episodically Flooded Field Mosquito Breeding Site

Example 2

Date Treated: Apr. 20, 2004
Location: Bishop, Warm Springs Rd.
Habitat: Pasture tail water
Species: O. melanimon
Site Size: 0.03 acre
Treatment: Pre-hatch; sprayed WP on ground
Dosage: 1.4 oz./acre
Water Depth: 6"-18"
Elapsed Days: 29
Sample size: 25
Mortality: 100%

Pre-Hatch Treatment in Episodically Flooded Field Mosquito Breeding Site

Example 3

Date Treated: Apr. 20, 2004
Location: Lone Pine
Habitat: Owens River overflow/seepage
Species: O. melanimon
Treatment: Pre-hatch; sprayed WP on ground
Dosage: 1.5 oz./acre
Site Size: 0.052 acre
Water Depth: 6"-18"
Elapsed Days: 57
Sample size: 25
Mortality: 96%

Pre-Hatch Treatment in Episodically Flooded Field Mosquito Breeding Site

Example 4

Date Treated: Jun. 29, 2004
Location: Bishop, Wye Rd., Big Cottonwood, N. of Five Cuts
Habitat: Pasture tail water
Species: O. melanimon
Site Size: 0.24 acre
Treatment: Pre-hatch; sprayed WP on ground
Dosage: 0.315 oz./acre
Water Depth: 6"-18"
Elapsed Days: 15
Sample size: 50
Mortality: 98%

Post-Hatch Treatment in Flooded Field Mosquito Breeding Site

Example 5

Date Treated: Jun. 28, 2004
Location: Bishop, Williams Cr Willow Draw
Habitat: Cattail choked irrigation tailwater slough
Species: O. melanimon
Site Size: 0.82 acre
Treatment: Post-hatch, spot sprayed WP into water on 50-100' intervals along 900' site
Dosage: 0.42 oz./acre
Water Depth: 12"-24"
Elapsed Days: 5
Sample size: 119
Mortality: 99%

The above specification, examples and data provide a complete description of the manufacture and use of the composition of the invention. Since many embodiments of the invention can be made without departing from the spirit and scope of the invention, the invention resides in the claims hereinafter appended.

We claim:

1. A slow release carbon and S-methoprene composition as a solid flowable particulate for mosquito control consisting essentially of an activated carbon particulate as the sole control release agent with a liquid S-methoprene impregnated therein, free of other slow release matrices and wherein said solid flowable particulate remains active in an aqueous use locus at least 100% longer than the S-methoprene; and wherein when said slow release composition is contacted with water it slowly releases the S-methoprene directly into the aqueous locus.

2. The composition of claim 1 wherein the amount of S-methoprene introduced into the carbon results in the release of an effective pest control concentration of S-methoprene in an aqueous site for at least 15 days.

3. The composition of claim 1 wherein the amount of S-methoprene introduced into the carbon results in the release of about 0.1 to 100 parts per billion of S-methoprene in the aqueous site for at least 30 days.

4. The composition of claim 1 wherein the amount of S-methoprene introduced into the carbon results in the release of about 0.1 to 50 parts per billion of S-methoprene in the aqueous site for at least 60 days.

5. The composition of claim 1 wherein the carbon and S-methoprene remains active at least 300% longer than the S-methoprene alone.

6. The composition of claim 1 wherein there are 0.1 to 1 parts of S-methoprene per each part by weight of the activated carbon.

7. The composition of claim 1 wherein the activated carbon has a particle size of about 5 μm to 2 mm.

8. The composition of claim 1 wherein the pesticide is technical S-methoprene.

9. A controlled release solid flowable carbon particulate S-methoprene composition for mosquito control, wherein said composition is substantially a matrix composition consisting essentially of an activated carbon as the sole control release agent and a S-methoprene liquid phase comprising S-methoprene impregnated therein, free of other slow release matrices wherein when said composite is contacted with environmental water, releases an effective amount of S-methoprene directly into the environmental water.

10. A method of controlling aquatic insects in a treatment locus, the method comprises selecting a treatment locus and distributing a slow release carbon and S-methoprene composition as a solid flowable particulate for mosquito control consisting essentially of an activated carbon particulate as the sole control release agent with a liquid S-methoprene impregnated therein, free of other slow release matrices and wherein said solid flowable particulate remains active in an aqueous use locus at least 100% longer than the S-methoprene; and wherein when said slow release composition is contacted with water it slowly releases the S-methoprene directly into the aqueous locus.

11. The method of claim 10 wherein the amount of S-methoprene introduced into the treatment locus results in the release of about 0.1 to 1000 parts per billion of S-methoprene in the treatment locus for at least 15 days.

12. The method of claim 10 wherein the amount of S-methoprene introduced into the treatment locus results in the release of about 0.1 to 100 parts per billion of S-methoprene in a treatment locus for at least 30 days.

13. The method of claim 10 wherein the amount of S-methoprene introduced into the treatment locus results in the release of about 0.1 to 50 parts per billion of S-methoprene in a treatment locus for at least 60 days.

14. The method of claim 10 wherein the carbon and S-methoprene combination remains active at least 300% longer than S-methoprene alone.

15. The method of claim 10 wherein there are 0.1 to 1 part of S-methoprene per each part by weight of activated carbon having a particle size of about 5 microns to 1 mm in a granule.

16. The method of claim 10 wherein there are 0.1 to 1 part of S-methoprene per each part by weight of activated carbon having a particle size of 1 mm to 4 mm in an extruded pellet.

17. The method of claim 10 wherein the treatment locus comprises a dry site.

18. The method of claim 10 wherein the treatment locus comprises a flooded site.

19. The method of claim 10 wherein the treatment site is intermittently dry and intermittently flooded.

20. The composition of claim 1 wherein the composition further comprises a diluent selected from the group consisting of sand, limestone, corncob, a plant fiber granule, diatomaceous earth, a clay and combinations thereof for even distribution into the use locus.

21. The composition of claim 9 wherein the composition further comprises a diluent selected from the group consisting of sand, limestone, corncob, a plant fiber granule, diatomaceous earth, a clay and combinations thereof for even distribution into the use locus.

22. A slow release solid flowable carbon and S-methoprene composition for mosquito control in an aqueous locus, consisting essentially of an activated carbon particulate as the sole control release agent with a liquid S-methoprene impregnated therein, free of other slow release matrices; and wherein there are 0.1 to 1.0 parts of S-methoprene per each part of the activated carbon, wherein when said slow release composition is contacted with water it slowly releases the S-methoprene.

23. The slow release carbon and S-methoprene of claim 22, wherein the activated carbon has a particle size of about 5 μm to 2 mm.

24. The slow release carbon and S-methoprene of claim 22, wherein the activated carbon has a surface area of 500-2500 $m^2/g$.

25. The slow release carbon and S-methoprene of claim 22, wherein the activated carbon has a surface area of 750-2000 $m^2/g$.

26. The slow release carbon and S-methoprene of claim 22, wherein the activated carbon has a surface area of 800-1750 $m^2/g$.

27. The composition of claim 1, wherein said composition is formulated as a water dispersible granule.

28. The composition of claim 9, wherein said composition is formulated as a water dispersible granule.

29. The slow release carbon and S-methoprene of claim 22, wherein said composition is formulated as a water dispersible granule.

* * * * *